United States Patent [19]

Wajaroff et al.

[11] 3,964,499

[45] June 22, 1976

[54] PROCESS FOR PERMANENTLY SHAPING HAIR

[75] Inventors: Theodor Wajaroff; Eugen Konrad, both of Darmstadt; Dieter Hoch, Pfungstadt, all of Germany

[73] Assignee: Wella AG, Darmstadt, Germany

[22] Filed: Oct. 15, 1974

[21] Appl. No.: 515,371

[52] U.S. Cl. .................................................. 132/7
[51] Int. Cl.² ......................................... A45D 7/04
[58] Field of Search ................ 132/7, 5; 424/71, 72

[56] References Cited
UNITED STATES PATENTS

| | | | |
|---|---|---|---|
| 2,615,828 | 10/1952 | Haefele | 132/7 |
| 2,865,811 | 12/1958 | Roesch | 424/71 |
| 3,144,391 | 8/1964 | Goff | 132/7 |
| 3,266,994 | 8/1966 | Reiss | 424/71 |

Primary Examiner—G.E. McNeill
Attorney, Agent, or Firm—Michael J. Striker

[57] ABSTRACT

Process for permanently waving or straightening human hair comprising the steps of pretreating the hair with a detergent solution containing an alkali metal- or ammonium sulfite, saturating the hair with an alkaline solution of a mercaptocarboxylic acid salt, winding the hair up on perforated hollow curlers or rollers having a diameter of 10–24 mm, rinsing the hair with water and removing the excess water from the hair, in separate steps or in a combined step treating the hair with peroxide and with a polymerizate to fix and set the same respectively, drying the hair, unwinding the hair from the curlers and combing the hair in the conventional manner to provide the desired hair fashion.

8 Claims, No Drawings

PROCESS FOR PERMANENTLY SHAPING HAIR

This invention relates to a multistage process for permanently waving or straightening human hair.

In order to produce a hair setting, a waving of the hair is necessary, the waving being achieved by means of a setting procedure carried out by one of two different methods and namely either according to the method of water waving or of permanent waving. In both of the aforesaid procedures, the hair is conventionally washed prior to undertaking the procedure.

According to the water waving procedure, the washed hair is moistened with an aqueous or aqueous-alcoholic resin solution, wound up on water setting curlers or rollers and then dried. Conventionally there are used for this purpose about 30–35 curlers or rollers having a diameter of about 15–40 mm. The winding time in this case amounts to about 40 minutes. The hair which as a result of this treatment has imparted thereto an inferior or limited swelling and softening is thereafter dried in the wound-up form. The excess resin remaining on the hair has the goal or purpose of stabilizing the hair in the newly waved form. The total procedure takes about 50 minutes if the time for the hair washing and the drying are included. The water waving thusly obtained is, depending on the hair length, moisture condition and mechanical stress it is subjected to, as for example by combing and brushing, lost after only a few hours, i.e., as soon as the hair is wet. In comparison to the wave appearance it had after the treatment it has returned to the original straight and strandy state.

Attempts have already been made to stabilize the water waving effects as for example through the use of a polymerizable substance or of other substances which has a crosslinking active effect on the hair keratin. These attempts have not up-to-date provided any practical approach in that the substances evaluated have been of questionable physiological effect and in addition have not produced any truly satisfactory results on the setting of the hair. The latter has been the case mostly because the action, i.e., effect of the substances employed remains confined to the surface of the hair.

For the permanent waving of the hair, the hair must be considerably more strongly softened and deformed than is possible with the water waving technique. in permanent waving, one proceeds through the use of certain suitable reduction agents which effect a chemical splitting of the disulfide bridges in the hair keratin. The waving rollers or curlers which are used in this connection are smaller than those used for the water waving and have a diameter of only about 6–8 mm, whereby the number of curlers required to be used for the averagely thick hair amounts to about 40–65 units. The winding time in this case amounts to about 25 minutes. For stabilizing and fixing the hair, an oxidizing agent is applied onto the hair in the wound-up form.

The process of the permanent waving is as a rule carried out in the following manner: After the hair has been washed, the hair is soaked or wet with the waving solution which customarily contains ammonium thioglycolate and has a pH ranging from 7.5–9.6, the hair is then wound up on rollers. After a working time of 15–20 minutes, the wound-up hair is rinsed with water and a fixing agent which is composed of an about 2% aqueous solution of hydrogen peroxide applied onto the hair. This is allowed to work for 5 minutes and then the hair is rewet with the fixing agent. After a working period of 5 minutes the hair is rinsed with water. In this manner there is obtained a stable, tight hair curl which remains stable against water and other usual hair treating agents. This tightly curled hair is not, however, suitable for producing an acceptable hair setting. It is necessary to further proceed so that after the permanent waving treatment as aforedescribed is completed, there is carried out a water waving as has been set out above. As a result of the further step of the water waving, the strongly curled hair is brought into more suitable condition for producing the desired setting or fashion. However, the thusly finished setting still evidences the disadvantages that under conditions of high humidity and wetness it undergoes changes in that it reverts to the small tight curls and therewith again resembles the hair after completion of the permanent waving step.

The process of permanent waving as heretofore known and practiced is a relatively complicated hair treatment which mainly has been carried out by trained, skilled craftsmen and in particular by hair stylists. The treatment takes on the average about 115 minutes to complete. If there is used during the working of the waving solution a dryer as heat source, which at the maximum reaches a temperature of 50°C, then the working time can be shortened by from 5 to 10 minutes. In this case the wound-up hair is covered up with a synthetic plastic hood the latter serving so that at the high temperatures involved a drying out of the hair is avoided.

As suitable agents for the permanent waving, there have been used sulfite-containing preparations. These are, however, today no longer considered acceptable for this objective because of the difficult condition associated with their use, in that in the alkaline range they are active only at higher temperatures of 70°–150°C and in the acid range they lead to an irreversible splitting of the disulfide bridges in the hair keratin.

Further in the permanent waving of hair, there have conventionally been used permanent waving curlers or rollers which have a larger diameter than those as above mentioned, and finally there have even been used the curlers or rollers employed in connection with water waving. In this manner there has been avoided the otherwise considerable time and work output associated with water waving and a more or less satisfactory permanent waving of the hair has still been obtained. By using curlers having a large diameter there is the advantage that only 30–35 curlers are required. Using the larger rollers therefore makes for a less troublesome and a more rapid processing. The curlers are in contrast to those of a conventional permanent waving hollow and perforated. Thereby in all of the following rinsing processes, the hair can be reached and wet from all sides as well as from inside of the roller. A process as has just been described cannot however be successfully carried out in practice. The basis for this is seen in that the strength of the hair waving decreases with increasing diameter of the curler and the waving thus produced then lasts only for a short time.

It has already been recommended that through the combination of a mercapto compound and a disulfide compound, the conventional oxidative fixing step can be avoided. The working of such combined agent is effective via a chemical equilibrium reaction between the reduced hair keratin, the mercapto compound and the disulfide and therewith in no case does this lead to a stable, long-lasting permanent waving. In addition an odor is imparted to the hair by the remaining mercapto compound and the disulfide. For obtaining a permanently lasting hair waving, there is no possibility of omitting an oxidative fixing step. This procedure has been used for many years and is physiologically unobjectionable if a suitable concentration of an oxidation agent is used and the agent uniformly distributed on the wound-up hair.

This requirement with respect to a permanent, loose curl wave hair setting exists not only for persons with straight hair but also exists for those having very strongly curled hair. In the latter case, it is necessary to subject the hair to what amounts to a decurling. The known methods for decurling have been conventionally undertaken using cream-form preparations which contain thioglycolates or soda lye as active agent. In this procedure the cream is applied onto the washed hair and then hair mechanically straightened by combing. When the desired degree of straightening has been reached, the cream is rinsed out of the hair with water and the hair in the case where a thioglycolate had been used further treated with an oxidation agent preferably hydrogen peroxide and in the case of the soda lye with an acid-containing agent. On completion of this procedure the water waving as has already been described is carried out. The time required for the permanent hair straightening is about the same as that for permanent waving. This generally conventional hair-straightening procedure has, however, the disadvantage that the hair is as a result of the required mechanical straightening very much over stretched with the consequence that hair breakage and hair fall-out occurs.

It has now most surprisingly been found that an extremely satisfactory permanent shaping of the hair can be obtained with significant time saving if the shaping is carried out in accordance with the process of the present invention.

According to the process of the invention, the hair in the case of an intended permanent waving is first washed with a sulfite-containing detergent which has a pH of 6–7.5. As sulfite there come into consideration, the water soluble alkali-metal sulfites as for example sodium and potassium sulfite as well as ammonium sulfite, the same being used in a concentration of 4–8 weight %. The detergent can be any anion active tenside as for instance from the class of alkylether sulfates, such as lauryl alcohol diglycolether sulfates, alkylaryl sulfonates such as lauryl benzene sulfonates or alkylarylether sulfates such as monylphenoxytetrapolyglycol sulfates. A preferred instance of a suitable tenside is sodium lauryl alcohol diglycol ether sulfate. After this washing of the hair, the hair is rinsed thoroughly. The entire treatment takes about 5 minutes. Then an aqueous solution of a mercaptocarboxylic acid salt, preferably an ammonium thioglycolate or thiolactate having a pH of from 7.5–9.6, obtained with alkaliniting agents, such as ammonia, ammonium carbonate, ammonium hydrogen carbonate or monoethanolamine, is applied onto the hair and the hair wound-up onto perforated hollow rollers or curlers having a diameter of 10–24 mm. The rolling takes about 10 minutes. The concentration of the mercaptocarboxylic acid salt in the solution amounts to 10–15 weight %. As a result of the action of the mercaptocarboxylic acid salt, there takes place not only the known splitting of the disulfide bridges in the hair keratin but at the same time because of the prior aforesaid sulfite treatment any formed organic thiosulfates (Bunte-salts) are split. This combined chemical action gives rise to a strong hair-shaping action and is furthered through the use of a hair drying hood.

The working time of the solution of the mercaptocarboxylic acid salt on the hair amounts to about 15 minutes and can be shortened to 10 minutes if a drying hood is used. In this latter case, the hair wound-up on the rollers is covered over with a synthetic plastic hood and thus at the higher temperatures involved a drying out of the hair is avoided. Thereafter the hair is rinsed out with water and the excess water removed with a hand towel. There can be realized a further advantage if the hair instead of being towel dried is dried out under a conventional dryer for about 5 minutes. There then follows an after-treatment in which the hair is first washed with a weak acid aqueous peroxide solution which contains about 0.5–2.0 weight % hydrogen peroxide. The peroxide is allowed to remain in contact with the hair for about 5 minutes and is then rinsed with water or water alcohol solution of a polymeric resin with the objective of stabilizing the hair setting. Thereafter the hair which is still on the rollers is dried and after having been unwound combined into the desired setting or fashion in the conventional manner.

As polymerizate for stabilizing, there come into consideration the known hair cosmetic polymers which act so as to form a film on the hair. These include natural and synthetic polymers as for instance vinyl polymerizates such as polyvinylpyrrolidone, polyvinylacetate, further polycrotonic acid and polyacrylic compounds such as polyacrylonitrile, acrylic acid or methacrylic acid polymerizates, basic polymerizates of esters of these acids (acrylic and methacrylic acids) with amino alcohols such as polydimethylaminoethylmethacrylate, salts or quaternization products of these basic polymerizates and as well, the corresponding copolymerizates of the aforesaid compounds, such as polyvinylpyrrolidone-vinylacetate, and polycrotonic acid-vinylacetate and polyvinylpyrrolidone-vinylacetate-dimethylaminoethylmethacrylate.

Especially suitable for use in the process of the invention is the copolymer of 50–70% vinylpyrrolidone, 30–40% vinylacetate and 2–6% dimethylaminoethylmethacrylate.

In accordance with another embodiment of the process of the invention, the after-treatment of the hair can be advantageously carried out so that in the same treatment step the hydrogen peroxide solution and the polymerizate solution are used, preferably with the two being combined into a single solution. In this case, this agent is applied onto the wound-up hair, the hair dried, unwound and then combed out into the desired hair setting or fashion. This embodiment as is clear permits a further reduction in time.

As a result of the permanent hair-shaping process of the invention, there is obtained an outstandingly loose, soft hair curl which heretofore could only be obtained with the water waving technique. However, in contrast thereto the curl now obtained is of unusual stability. The hair curling is outstandingly resistant to humidity, mechanical influences, subsequent hair washing or treatment with any of the conventionally used hair cosmetics. Further advantages lie in that the resultant hair curling has the appearance of a genuine natural hair curl and retains without resorting to the use of curlers after subsequent hair washing and other usual hair treatments its curled appearance. This has not been the case in connection with the heretofore carried out water waving.

In an analogous manner and using the same agents as aforedescribed, the permanent waving process of the invention can also be used on strongly curled hair to decurl it and to form loose curls characterized by the aforesaid stability. For this purpose the tightly curled hair is first washed with a sulfite-containing detergent having a pH of 6–7.5 and then rinsed with water. Thereafter the hair is wet with the waving solution which contains a mercaptocarboxylic acid salt and has a pH of 7.5–9.6 obtained with alkaliniting agents such as ammonia, ammonium carbonate, ammonium hydrogen (carbonate or monoethanolamine, and the hair then wound-up on the large curlers as aforedescribed. After the shaping solution has acted on the wound-up hair for 15 minutes (the time can be shortened to 10 minutes by using a drying hood), the hair is rinsed with water and treated for about 5 minutes with an acid hydrogen peroxide solution, i.e., oxidatively fixed. The hair is then rinsed out with water and a solution of a polymerizate applied. Finally the hair is dried, unwound and combed in conventional manner into the desired hair fashion.

As in the case of the permanent waving, the hair straightening can be carried out using both the hydrogen peroxide and polymerizate combined in a single treatment agent. In this case this combined agent is applied onto the hair, the hair dried, unwound from the curlers and combined into the setting.

The process of the invention improves the quality of the hair shaping obtained, also considerably shortens the time required for the treatment by up to about 40% and in addition is without any attendant risks and is so simple that even a non-experienced person can carry the same out.

The following Example is given in order to more fully illustrate the invention and is equally effective to illustrate waving or straightening of hair.

The Example is illustrative only and is not to be construed as in anywise limiting the scope of the invention. In the Example all of the percentage values are percents by weight unless otherwise specifically indicated.

EXAMPLE

Stage 1

A solution having the following composition:
7.1 g aqueous solution of ammonium sulfite (35%)
25.0 g aqueous solution of sodium lauryl alcohol diglycolether sulfate (28%)
0.2 g perfume oil
7.7 g water and having a pH of 6.5 was applied onto hair which had been previously wet with water so that the hair was thoroughly foamed through with the solution and then the solution was rinsed out with water. The duration of the treatment amounted to about 5 minutes.

In place of the aforesaid solution, there can also be used in the first stage the following solution:
25.0 g aqueous solution of ammonium lauryl sulfate (35%)
10.0 g aqueous solution of ammonium sulfite (35%)
5.0 g urea
5.0 g isopropyl alcohol
0.3 g perfume oil
4.7 g water This latter solution had a pH of 6.8 and was used as above described. The duration of the treatment amounted to 5 minutes.

Stage 2

The hair was thoroughly wet with a solution having the following composition:
16.4 g aqueous solution of ammonium thiolactate (50%)
4.0 g ammoniacal solution (25%)
0.3 g oleic acid pentaerithritepolyglycolether
0.3 g perfume oil
39.0 g water The solution had a pH of 9.6. The hair was then wound-up on large perforated rollers or curlers having a diameter of 10–24 mm. Following the winding-up of the hair, the solution was allowed to act thereon for 15 minutes. The hair was then rinsed out with water, the excess water removed with a hand towel. Instead of using a hand towel, the hair could be dried for 5 minutes under a drying hood.

In place of the above solution there could also be used in Stage 2 a solution having the following composition:
18.0 g aqueous solution of ammonium thioglycolate (50%)
4.2 g ammonium hydrogen carbonate
0.5 g ammonium carbonate
2.0 g urea
0.4 g octylphenol + 20 mol ethyleneoxide-oxyethylated
0.3 g perfume oil
54.6 g water The solution had a pH of 8.6 and was used as aforedescribed, however with the difference that there was employed during the working of the solution a drying hood. This had the effect of shortening the working time to only 10 minutes.

Stage 3

An oxidizing solution having the following composition:
14.3 g hydrogen peroxide solution (35%)
0.5 g o-phosphoric acid (85%)
1.0 g isooctylphenol + 10 mol ethyleneoxide-oxyethylated
0.2 g perfume oil
64.0 g water was before use diluted with warm water up to a volume of 1 liter. The wound-up hair was treated with a dilute solution for a period of 5 minutes.

Instead of this foregoing solution there could also be used in Stage 3 a solution of the following composition:
22 g percarbamide-powder (35% content of $H_2O_2$) dissolved before use in 500 ml warm water. This solution is used in the same manner as the aforedescribed solution.

Stage 4

Thereafter one of the hair-fixing solutions a–d as hereinafter set out which prior to use was diluted with water up to 125 ml was applied onto the still wound-up hair:

a. 6.0 g 50% solution of a copolymerizate of 60% vinylpyrrolidone, 36% vinylacetate and 4% dimethylaminoethylmethacrylate in ethanol
0.1 g perfume oil
0.1 g cetyl pyridinium chloride 3.0 g ethanol
0.8 g water
b. 8.0 g 50% solution of a copolymerizate of 60% vinylpyrrolidone, 36% vinylacetate and 4% dimethylaminoethylmethacrylate in ethanol
0.1 g perfume oil
0.2 g cetyl trimethylammonium chloride
1.7 g isopropanol
c. 6.0 g 50% solution of a copolymerizate of 60% vinylpyrrolidone, 36% vinylacetate and 4% dimethylaminoethylmethacrylate in ethanol
0.1 g perfume oil
0.1 g cetylpyridiniumchloride
3 g ethanol
0.5 g pyroracemic acid
0.3 g water
d. 6.0 g 50% solution of a copolymerizate of 60% vinylpyrrolidone, 36% vinylacetate and 4% dimethylaminoethylmethacrylate in ethanol
0.1 g perfume oil
0.1 g cetyltrimethylammonium chloride
3.0 g ethanol
0.005 g methyl violet
0.8 g water Thereafter the hair was dried, unwound from the rollers and in the conventional manner combed into the desired hair fashion. White hair treated with solution (d) had simultaneously imparted thereto a blue tone.

In another form of carrying out the process of the invention Stages 3 and 4 can be combined so that the treatment is carried out with the solution having both setting and oxidizing components combined therein. This form of the invention can be carried out using 30–50 ml (depending on the amount of hair) of a solution having the following composition:

4.0 g 50% solution of a copolymerizate of 60% vinylpyrrolidone, 36% vinylacetate and 4% dimethylaminoethylmethacrylate in ethanol
0.2 g perfume oil
0.1 g cetylpyridiniumchloride
0.2 g octylphenol + 20 ml ethyleneoxide oxyethylated
5.7 g hydrogen peroxide solution (35%)
0.1 g salicylic acid
89.7 g water As in the previous embodiment, this solution was applied onto the wound-up hair, the hair then dried, unwound off of the rollers and combed in the conventional manner into the desired fashion.

We claim:
1. Process for permanently waving or straightening human hair comprising the steps of pretreating the hair with a detergent solution containing an alkali-metal or ammonium sulfite, wetting the hair with an alkaline solution of a mercaptocarboxylic acid salt, winding the hair up on perforated hollow curlers having a diameter of 10–24 mm, rinsing the hair with water and removing the excess water from the hair, in separate steps or in a combined step treating the hair with hydrogen peroxide for fixing the same and with a polymerizate for setting the same, drying the hair, unwinding the hair, from the curlers, and combining the hair in accordance with a desired hair fashion.

2. Process according to claim 1 wherein there is used in said first step sodium, potassium or ammonium sulfite having a concentration of 4–8 weight % in said solution and a pH of 6.0–7.5.

3. Process according to claim 1 wherein there is used as said detergent an anion active tenside.

4. Process according to claim 3 wherein as anion active tenside there is used an alkylether sulfate, alkylaryl sulfonate or alkylarylether sulfate.

5. Process according to claim 1 wherein as mercaptocarboxylic acid salt there is used the ammonium salt of thioglycolic acid or thiolactic acid.

6. Process according to claim 1 wherein the excess water remaining on the hair is removed by drying with a hand towel or by maintaining the hair under a dryer for 5 minutes.

7. Process according to claim 1 wherein as polymerizate a copolymer of 50–70% vinylpyrrolidone, 30–40% vinylacetate and 2–6% dimethylaminoethylmethacrylate is used.

8. Process according to claim 7 wherein said copolymer is composed of 60% vinylpyrrolidone, 36% vinylacetate and 4% dimethylaminoethylmethacrylate.

* * * * *